United States Patent [19]

Lahme et al.

[11] 4,229,104
[45] Oct. 21, 1980

[54] MIXING CUVETTE

[75] Inventors: Gerhard Lahme, Quickborn; Dieter Sölter, Hamburg; Hermann Bohnsack, Halstenbek, all of Fed. Rep. of Germany

[73] Assignee: Eppendorf Gerätebau Netheler & Hinz GmbH, Hamburg, Fed. Rep. of Germany

[21] Appl. No.: 884,118

[22] Filed: Mar. 7, 1978

[30] Foreign Application Priority Data

Mar. 12, 1977 [DE] Fed. Rep. of Germany ....... 2710889

[51] Int. Cl.² .......................................... G01N 21/24
[52] U.S. Cl. .................... 356/246; 356/427; 356/440
[58] Field of Search ...................... 356/246, 427, 440; 250/576; 422/72, 99, 102

[56] References Cited

U.S. PATENT DOCUMENTS

| 3,627,432 | 12/1971 | Bergmann | 356/246 |
| 3,814,522 | 6/1974 | Clark et al. | 356/246 |

Primary Examiner—John K. Corbin
Assistant Examiner—Matthew W. Koren
Attorney, Agent, or Firm—Toren, McGeady and Stanger

[57] ABSTRACT

A mixing cuvette for mixing different substances introduced therein by high speed rotary mixing, the cuvette being of a relatively small capacity but defining a great filling height. The cuvette body is elongated and encloses an internal cavity defined in its upper portion by a peripheral side wall that merges into a polygonal multi-surface lower portion. This cavity is open at the top and closed at its bottom. The lower portion includes a measuring region with a pair of opposite planar parallel surfaces through which may be directed a photometric measuring beam.

10 Claims, 6 Drawing Figures

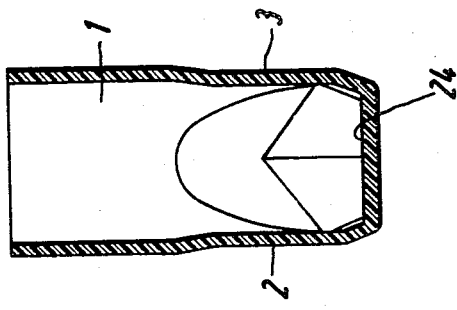
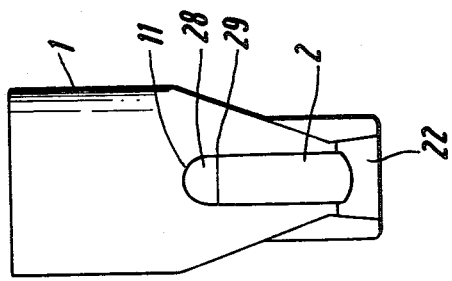
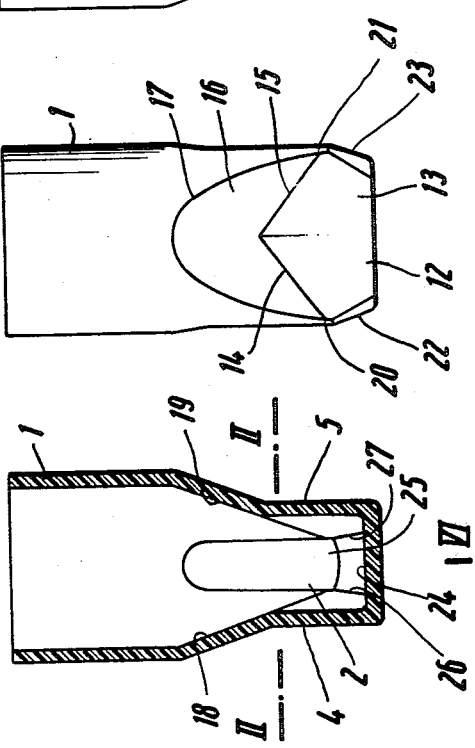
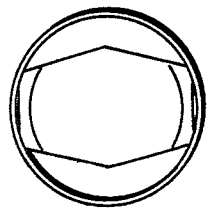
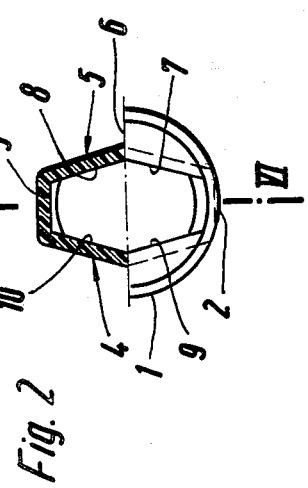

MIXING CUVETTE

The present invention relates to a mixing cuvette for mixing substances by rotational mixing, particularly by high speed circular horizontal movement of the cuvette which is formed with a small capacity and great filling height within the region of at least one measuring distance across the cuvette whereby there is predetermined a wall spacing in the measuring direction.

With respect to the term measuring distance used above in relation to the mixing cuvette, it is pointed out that the spacing in measuring directions is preferably 10 mms. In mixing cuvettes of this type various inputs may likewise be mixed by either rotating the cuvette to and fro through an angle of almost up to 360° about its vertical center axis or by effecting an incremental continuous rotational movement about this center axis whereby the pulses between standstill and rotation are supposed to agitate the contents of the mixing cuvette for mixing. In this arrangement, the components introduced into the cuvette are supposed to be accelerated differently at the inner wall surfaces and to be intermixed by turbulent flow.

The great filling height with a small volume is intended to allow investigations of minimum quantities which have, likewise, to be intermixed. For mixing, it is likewise known to employ, in cuvettes, agitator rods with pedal-shaped ends, and to rotate these agitator rods with respect to the cuvette, i.e. to virtually stir the contents. This requires a considerable inner cross-section so that considerable amounts of sample are necessary. Moreover, this arrangement is expensive because apart from the rotary drive for the rotary member, whether this member is the agitator rod or the cuvette there are necessary movements for introducing the agitator rods into the cuvette or respectively sliding the cuvette onto the agitator rod from below. Dispensing is correspondingly necessary whereby it must be furthermore assumed that there are still required subsequent transfers to the measuring station. When not replacing or cleaning the agitator rod, there will arise additionally contamination errors between subsequent samples of various compositions.

It is likewise known to provide a rake extending upwardly in the axial direction from the bottom of an inherently cylindrical cuvette whereby this rake causes disturbances and agitation upon rotation of the cuvette about its axis and thereby leads to mixing of the contents. Such a rake prevents measurements in its region which could only be effected above the rake whereby is entrained again the disadvantage that a considerable quantity of fluid is required.

In the above described mixing operation there arises the basic difficulty that the demands for a small sample volume at a sufficient filling level and for a satisfactory mixibility cannot be realized jointly to any sufficient degree. Additionally, there must be taken into account the demand of an easy temperature control of the sample.

It is, therefore, an object of the present invention to provide a novel and improved mixing cuvette.

It is another object of the present invention to provide an improved mixing cuvette of a suitable configuration for meeting the requirements set forth above to such a degree so as to permit a substantially more progressive microanalysis technique.

It is still another object of the present invention to provide a cuvette that allows a rapid mixing by rotational movement with respect to its longitudinal axis whereby a mixing cuvette of the type as stated at the outset of the present specification shall be designed so as to allow a measurement immediately subsequent to a mixing operation by rotation with respect to the longitudinal axis and even in the measuring distance, and that thereby may be investigated small quantities and there will be obtained an optimum mixing under the indicated conditions.

In accordance with the present invention, these objects are achieved by the fact that the interior of the cuvette is enlarged perpendicularly of the measuring direction in the measuring region between opposing parallel wall portions in a central region of a center axis defined by the measuring direction, whereby the side walls between the wall portions consist interiorly of planar surface portions including an obtuse angle in an engagement region in the area of the longitudinal center line. Surprisingly, it has been discovered that optimum conditions are not obtained by e.g. a rectangular or circular cross-sectional configuration of the interior cavity but by the indicated configuration allowing a great filling height with a small base surface and ensuring good mixing of components within a short time. In a particularly advantageous embodiment, this obtuse angle is about 140°. Suitably, the wall portions through which the measurement is effected are of a width on the order of magnitude of 3 mms.

In an advantageous embodiment the cuvette includes a lower inner bottom surface of the order of magnitude of about 47 square millimeters adjacent the measuring region. In a cuvette of this type there will be obtained e.g. a filling height of 10.5 mms for a volume of 500 microliters.

The above described configuration is particularly suitable for treating small volumes. Thereby may be left out of account that, likewise, other cross-sectional configurations may be imagined when admitting larger base surfaces whereby, however, are either required larger fluid quantities for disturbance-free working, or with the same fluid quantities may be obtained smaller filling heights which is a disadvantage for photometrical measurements.

It is preferred that the mixing cuvette, in its upper region, is of a configuration that is adapted to be enveloped by an imaginary cylinder. This cylindrical configuration is advantageous for handling the cuvettes in devices, for filling and likewise for simple manufacture. Suitably, it is included that the upper region is of a cylindrical configuration and this cylindrical shape includes, in its lower region, retracted portions whereby the wall portions provided for the passage of the photometric beam include planar parallel faces extending upwardly up to the cylindrical region that is substantially within the cylindrical contours.

Another embodiment provides that within an imaginary cylinder there is retained likewise at the top a "cornered" and particularly a polygonal configuration.

In the preferred embodiment side walls in the lower region opposite the upper cylindrical region or region disposed within an imaginary cylinder are inclined inwardly whereby result downwardly and outwardly inclined delimiting lines, with respect to the wall portions extending substantially parallel of the cuvette axis, at the upper edge of outer side wall portions meeting at obtuse angles. This provides not only a small volume, particularly within the measuring region, but likewise easy introducibility into the measuring region of fluid to be treated and surprisingly further improved mixing results which may be observed always when wetting not only vertical but likewise inclined and upwardly and outwardly flaring wall portions at least during the mixing operation. The measuring region in this advantageous embodiment is suitably of a rhombic cross-section, with the bevels defined by the wall portions provided for the passage of the photometric beam in its longitudinal axis.

The introduction of the sample fluid into the measuring region as mentioned above may be improved by the expedient that above the surface portion that is parallel to the axis are provided, toward the upper region, upwardly enlarged portions forming a funnel-shaped transition zone toward the measuring region.

In an advantageous embodiment the wall portions below the measuring region are inclined and retracted inwardly and define, in this region, faces having lower outwardly flaring lateral edges. This results in a further reduction of volume and an improvement of the mixing properties of the cuvette.

In the following, the present invention will be described more in detail with reference to several embodiments shown in the appended drawings wherein FIG. 1 is a lateral sectional view of a mixing cuvette in accordance with a preferred embodiment of the present invention;

FIG. 2 is a partially sectional top view of the cuvette along the line II—II of FIG. 1;

FIG. 3 is a bottom view of the cuvette;

FIG. 4 is a lateral elevational view of FIG. 1;

FIG. 5 is a face elevational view of FIG. 1; and

FIG. 6 is a cross-sectional view along the line VI—VI of FIG. 2.

The cuvette includes an outwardly laterally closed wall with an upper region 1 and a lower measuring region 25. This wall is closed at its bottom by a bottom that defines a lower bottom surface 24 of the measuring region.

The illustrated cuvette is in its upper region 1 of a cylindrical cross-section, although this is not required for the present invention. In this context it is included that this region may in cross-section be likewise polygonal in approximation to the contour of a cylinder, and optionally may be likewise rectangular.

For facilitating operation or handling, this upper region 1 is of an enlarged cross-section with respect to the lower measuring region and is e.g. of a diameter of the order of magnitude of between 5 and 12 mms. The enlarged cross-section in the upper region is likewise a pre-requisite that in the intermediate and lower regions are likewise present, apart from vertical wall portions, inclined inwardly and outwardly extending wall portions which in combination with the vertical wall portions improve the mixing properties of the cuvette. The upper diameter is dependent upon the length of the measuring distance of the lower region. This length may be e.g. 10 mms whereby the enlarged upper but substantially radially symmetrical region is likewise in this order of magnitude.

For the measuring distance the cuvette is retracted inwardly at opposing sides with respect to the condition of providing a minimum volume. The wall portions 2, 3 extending perpendicularly of the measuring direction and being of equal thickness extend substantially within the contour of the upper region. In a cylindrical embodiment are provided planar parallel bevels of equal wall thicknesses for forming the wall portions 2, 3. The width of these wall portions is on the order of magnitude of about 3 mms. The wall portions 2, 3 extend up to about half the height of the cuvette.

The median perpendicular through the wall portions 2, 3 is the so-called longitudinal axis of the cross-section in the measuring region. The vertical side walls retracted with respect to the upper region are indicated in FIGS. 1 and 2 by the reference numerals 4 and 5. These side walls consist of interiorly flat surface portions 7, 8 and respectively 9, 10 that meet at an obtuse angle in the region of the longitudinal center at 6. The degree of retraction corresponds e.g. to 1/6 of the diameter of the upper region.

From FIGS. 1 and 5 may be seen that the wall portions 2, 3 join at their tops along a curve that corresponds to the line 11 the cylindrical region. The upper part 28 of the wall portions 2, 3 may likewise be bent outwardly as indicated at 29 and merge into the cylindrical region. The outer sides 12, 13 of the surface portions 7–10 which include an interiorly open obtuse angle merge, as may be seen in FIG. 4, e.g. along the straight lines 14 and 15 respectively inclined upwardly toward the center, into a portion 16 that forms the transition to the upper and e.g. cylindrical region and delimited thereagainst by the curve 17. Correspondingly, the inner surfaces such as 18, 19 define a tapered or respectively funnel-shaped transition into the lower or respectively measuring region of the cuvette which provides for a great filling height with small volumes or respectively a small bottom surface. As may be seen, the straight lines 14, 15 and the curve 17 meet at 20, 21. Below this level is disposed a portion 25 delimited on all sides by surfaces extending parallel to the axis whereby particularly the rhombic cross-section with the bevels in the form of wall portions 2, 3 is provided at the ends of the longitudinal axis. The measuring region 25 in which is effected the photometrical measurement is disposed intermediate the planar parallel parts of the vertical wall portions 2 and 3. Spaced from the points 20, 21, i.e. below the measuring region, the wall portions 2, 3 are inclined inwardly so that there result the inwardly retracted faces 22, 23 above the lower bottom surface 24. These faces may have a slight outward convex curvature. By retracting these faces 22, 23 downwardly and the surface portions 7, 8 at an angle to the longitudinal axis result at the sides, e.g. at the face 22 (FIG. 1) downwardly and outwardly inclined lateral edges 26, 27. Since the inclined faces are of only a small height immediately above the bottom surface 24, the actual measuring region 25 constitutes a cavity in which the substances are restricted to a minimum volume for carrying out the measuring operation. The contour of this cavity contributes in ensuring good mixibility despite of a small volume.

At least during the mixing operation suitably not only vertical but likewise upwardly and outwardly inclined wall portions 2, 3 or respectively the surfaces 18, 19 are wetted.

The embodiments of the invention in which an exclusive property or privilege is claimed are defined as follows:

1. A mixing cuvette suitable for the mixing of substances by rotational motion, particularly high speed circular horizontal movement thereof, said cuvette comprising: an upward generally cylindrical portion and a lower measuring portion contiguous therewith; a longitudinal central axis extending through said upper and lower portions; a bottom wall containing an inner bottom surface defining the lower termination of said lower portion; a pair of opposed generally planar parallel wall portions extending upwardly from said bottom wall defining therebetween a photometric measuring region of said cuvette, with a photometric measuring direction of the cuvette being defined to extend across said measuring region perpendicularly to said opposed wall portions; and a pair of V-shaped side walls each extending between said opposed parallel wall portions on opposite sides of said measuring region; each of said V-shaped side walls defining an interior surface of said lower portion of said cuvette having an apex located on a plane containing said longitudinal central axis and extending perpendicularly to said measuring direction; each of said interior surfaces including surface portions extending from said apex and defining an obtuse angle therebetween to effect an enlargement of the interior of said cuvette through a central region of said measuring portion extending perpendicularly to said measuring direction.

2. A mixing cuvette as defined in claim 1 wherein said obtuse angle is about 140°.

3. A mixing cuvette as defined in claim 1 wherein said wall portions are of a width on the order of magnitude of 3 mms.

4. A mixing cuvette as defined in claim 1 wherein the inner bottom surface (24) is of a size on the order of magnitude of about 47 square millimeters.

5. A mixing cuvette as defined in claim 1 wherein said upper region (1) is of a cylindrical configuration and this cylindrical shape includes, in its lower region, retracted portions whereby the wall portions (2, 3) provided for the passage of the photometric beam include planar parallel faces extending upwardly up to said cylindrical region substantially within the cylindrical contours.

6. A mixing cuvette according to claim 1 wherein said V-shaped side walls each have a V-shaped upper terminal edge having edge portions on opposite sides of said apex extending downwardly away from said apex.

7. A mixing cuvette as defined in claim 1 wherein said measuring region is formed with a rhombic cross section, with said lower portion of said cuvette including a pair of slanted wall portions extending between said bottom wall and said opposed parallel wall portions to form bevels provided for the passage of a photometric beam through said measuring region.

8. A mixing cuvette as defined in claim 7 further including transition wall portions extending between said upper portion of said cuvette and said V-shaped side walls in order to form a funnel-shaped transition zone tapering inwardly from said upper portion to said measuring region of said cuvette.

9. A mixing cuvette according claim 7 wherein said slanted wall portions have lower outwardly flaring lateral edges.

10. A mixing cuvette comprising an upper portion and a lower portion, a longitudinal central axis extending through said upper and lower portions, a pair of opposed wall portions extending generally parallel with said longitudinal axis and defining therebetween a photometric measuring region of said cuvette, with a photometric measuring direction of the cuvette being defined to extend across said measuring region, a pair of side walls each extending between said wall portions on opposite sides of said measuring region, said side walls being configured to define a pair of opposed concave interior surfaces of said measuring region, said concave interior surfaces being shaped to effect an enlargement of the interior of said cuvette through a central region of said measuring portion extending perpendicularly to said measuring direction.

* * * * *